United States Patent
Müller

(10) Patent No.: US 6,838,077 B2
(45) Date of Patent: Jan. 4, 2005

(54) OIL-FREE COSMETIC OR DERMATOLOGICAL PREPARATIONS WITH A CONTENT OF SOLID AND LIQUID UV FILTER SUBSTANCES

(75) Inventor: Anja Müller, Rümpel (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 10/188,790

(22) Filed: Jul. 2, 2002

(65) Prior Publication Data

US 2003/0053965 A1 Mar. 20, 2003

Related U.S. Application Data

(63) Continuation of application No. PCT/EP00/12823, filed on Dec. 15, 2000.

(30) Foreign Application Priority Data

Jan. 5, 2000 (DE) .......................... 100 00 211

(51) Int. Cl.$^7$ ............................ A61K 7/42; A61K 7/44; A61K 7/00
(52) U.S. Cl. .......................... 424/59; 424/60; 424/400; 424/401
(58) Field of Search ............................ 424/59, 60, 400, 424/401

(56) References Cited

U.S. PATENT DOCUMENTS

| | | |
|---|---|---|
| 4,663,157 A | 5/1987 | Brock |
| 5,041,281 A | 8/1991 | Strobridge |
| 5,207,998 A | 5/1993 | Robinson et al. |
| 5,306,485 A | 4/1994 | Robinson et al. |
| 5,849,274 A | 12/1998 | Gers-Barlag et al. |
| 5,914,102 A | 6/1999 | Fowler et al. |

OTHER PUBLICATIONS

Swarbrick, James, DSc, PhD, "Coarse Dispersions," Remington's Pharmaceutical Sciences, 1975, pp. 338–339, Mack Publishing Company, U.S.A.

International Search Report from corresponding International Application PCT/EP00/12823, dated Oct. 9, 2001.

*Primary Examiner*—Shelley A. Dodson
(74) *Attorney, Agent, or Firm*—Alston & Bird LLP

(57) ABSTRACT

The present invention includes oil-free cosmetic or dermatological emulsions that include a water phase and at least one UV filter substance which is liquid at room temperature as a further phase, where the difference in density between the UV filter phase and the water phase (determinable using a computerized digital density meter of the type DMA 45 from Chempro/PA at 25° C.) is not greater than 0.01 g·cm$^{-3}$. The present invention further includes processes for the preparation of oil-free emulsions.

20 Claims, No Drawings

OIL-FREE COSMETIC OR DERMATOLOGICAL PREPARATIONS WITH A CONTENT OF SOLID AND LIQUID UV FILTER SUBSTANCES

CROSS-REFERENCE TO RELATED APPLICATIONS

This is a continuation application of PCT/EP00/12823, filed Dec. 15, 2000, which is incorporated herein by reference in its entirety, and also claims the benefit of German Priority Application No. 100 00 211.0, filed Jan. 5, 2000.

FIELD OF THE INVENTION

The present invention relates to oil-free cosmetic or dermatological preparations with a content of solid and liquid UF filter substances, preferably in the form of cosmetic or dermatological light protection preparations.

BACKGROUND OF THE INVENTION

Cosmetic preparations are essentially used for skincare. The skin is the largest human organ. Among its many functions (for example for heat regulation and as a sensory organ), the barrier function, which prevents the skin (and thus ultimately the entire organism) from drying out, is by far the most important. At the same time, the skin acts as a protective device against the invasion and the absorption of external substances (e.g. dirt, chemicals, microorganisms).

The main aim of cosmetic skincare is therefore to strengthen or restore this natural function of the skin as a barrier against environmental influences and against the loss of endogenous substances (as well as water, also natural fats, electrolytes etc.).

Another aim of skincare is to compensate for the loss by the skin of lipids and water caused by daily washing. This is particularly important if the natural regeneration ability is inadequate. Furthermore, skincare products should protect against environmental influences, in particular against sun and wind, and delay skin aging.

By far the most important type of product in the field of skincare compositions are emulsions. Emulsions are generally to be understood as meaning heterogeneous systems which consist of two liquids which are immiscible or miscible with one another only to a limited extent, which are usually referred to as phases. In an emulsion, one of the two liquids is dispersed in the other liquid in the form of very fine droplets.

Cosmetic or dermatological emulsions of the prior art consist of at least one fatty phase (fats and mineral oils, fatty acid esters, fatty alcohols etc.) and at least one water phase (water, glycerol, glycols etc.) which are dispersed in one another in the form of very fine droplets with the help of emulsifiers. If the oil phase is finely distributed in the water phase, then this is an oil-in-water emulsion (O/W emulsion, e.g. milk). The basic character of an O/W emulsion is defined by the water, i.e. it is less greasy on the skin, has more of a matting effect and absorbs more rapidly into the skin than a W/O emulsion.

The lipophilic phase of a bodycare emulsion usually comprises a mixture of oils, fats and waxes, the composition of which is to essentially influence the product-determining properties such as skincare and feel on the skin. Corresponding to the central importance of the oils, fats and waxes, a very broad range of these substances is commercially supplied and used.

For the purposes of this specification, oils, fats and waxes are referred to collectively as "oils" or "oil components".

Accordingly, the terms "oils" and "oil components" for the purposes of the present invention are to be understood as meaning the following compounds:

hydrocarbons
triglycerides
fatty esters or ester oils

The group of hydrocarbons includes the various fractions of mineral oils and fats, and also squalene and squalane. A common feature of the compounds of this group is that they are constructed from straight-chain or branched-chain hydrocarbons. The hydrocarbons include, for example, paraffin oil, vaseline, hard paraffin, microcrystalline wax, mineral oils, ozokerite and ceresine.

Triglycerides are complete esters of glycerol with fatty acids. The compounds of this group usually form an essential constituent of lipid-containing cosmetic preparations. This group includes the naturally occurring (vegetable and animal) oils (for example avocado oil, olive oil, corn oil, mink oil, castor oil, soybean oil, sunflower oil and sesame oil, to name but a few) and fats (e.g. Japan wax, cocoa butter and the like). Synthetic triglycerides which are prepared by esterification of fatty acids with glycerol also belong to this group.

Through the esterification of fatty alcohols with organic mono-, di- and polycarboxylic acids or short-chain alcohols with long-chain fatty acids, it is possible to prepare a large number of fatty esters which are customarily used very widely in cosmetic preparations. This group includes, inter alia, monocarboxylic esters (for example butyl stearate, cetyl palmitate, decyl oleate, 2-ethylhexyl palmitate, hexyl laurate, isopropyl isostearate, lanolate, laurate, linoleate, palmitate, stearate, to name but a few), dicarboxylic esters (e.g. diisopropyl adipate, cetyl, lauryl and myristyl lactate and diglycerol esters of caprylic, capric and succinic acid and the like), and alkyl benzoates.

The use of oil components in cosmetic or dermatological preparations is acceptable per se. Nevertheless, oils, like ultimately every chemical substance, can in individual cases cause allergic reactions or reactions based on hypersensitivity of the user. Thus, for example, various oils are also suspected, with exposure to sunlight, of triggering photodermatoses, which are also referred to as "Mallorca acne".

Moreover, oil-containing cosmetic and dermatological preparations have the disadvantage that they have comedogenic activity, i.e. they can cause or aid the formation of skin symptoms which are characterized by noninflammatory and inflammatory papules. Starting from blocked hair follicles (comedones), such skin symptoms can lead to pustule, abscess and scar formation. The most common is Acne vulgaris, which occurs primarily in puberty. Causative conditions are the keratinization and blocking of the hair follicle opening.

Moreover, oil-containing cosmetic and dermatological preparations can produce a greasy and sometimes sticky impression on the skin and are difficult to distribute, particularly on skin covered with hair. In individual cases, they may therefore not even be marketable since they are unacceptable to or are viewed negatively by the consumer.

However, in cosmetic or dermatological light protection preparations of the prior art in particular, at least when high sun protection factors (e.g. greater than SPF 15) are to be achieved, oils have hitherto been necessary to dissolve lipophilic filter substances.

Although, when viewed from a thermodynamic viewpoint, emulsions are unstable systems, it is possible to prepare emulsions which are stable for years. An emulsion is described as stable if, over a predefined period of time, no measurable temporal or spatial changes in the droplet size distribution can be established.

The stability or instability of emulsions depends on a variety of factors. Firstly, the water phase of a W/O emulsion tends, for example, toward sedimentation since the water and oil phases have different densities. The oil phase of an O/W emulsion, accordingly, has a tendency toward creaming.

In addition, because of the forces of attraction between the finely distributed droplets of the disperse phase, drop aggregation can result, where the individual droplets of an aggregate remain initially separate from one another by a thin film of the continuous phase. In this case, the original droplet size distribution only appears to change and can in this case be restored by stirring or shaking.

However, the droplets which are in contact can, moreover, also coalesce, which leads to a real change in the droplet size distribution, which can only be changed back by inputting energy. This phenomenon is referred to as coalescence. The more viscous the outer phase of the emulsion, the more slowly the process of coalescence proceeds.

The processes described can occur individually or together. One process often initiates or intensifies the other. Thus, for example, the formation of aggregates in O/W emulsions accelerates creaming of the oil phase. If the disperse state of an emulsion is partially or even completely lost, then the two phases separate, and this is referred to as emulsion breaking.

Accordingly, the stabilization of emulsions over a relatively long period of time requires auxiliaries which prevent separation of the two phases, or at least delay it until the emulsion has fulfilled its intended purpose.

These auxiliaries should firstly stabilize the interface by preventing the droplets of the disperse phase from coalescing. In the ideal case, these substances moreover effect repulsion of the droplets, which prevents them from contacting, thus avoiding agglomeration (aggregate formation).

Secondly, auxiliaries are used to counteract creaming or sedimentation of the phases.

Emulsifiers are interface-active substances which are able to prevent the interfacial tension between external and internal phase by positioning themselves preferably at the interface between these two phases. This is made possible as a result of their amphiphilic molecular structure: emulsifiers have at least one polar (hydrophilic) group and at least one nonpolar (lipophilic) group. As a result, they are soluble both in the hydrophilic phase and in the lipophilic phase. The part which is more soluble in the corresponding phase protrudes into this phase and as a result lowers the interfacial tension between the two phases.

The attempt to classify emulsifiers is difficult since they belong to categories which are very different in chemical terms. The more quickly an emulsifier lowers the interfacial tension and the lower the equilibrium value of the interfacial tension, the more effective the emulsifier.

Moreover, emulsifiers also stabilize emulsions as a result of the formation of interfacial films and thus "physical" barriers, as a result of which aggregate formation and coalescence of the emulsified particles is prevented. As a result of the positioning of the emulsifier at the interface, the droplets either become charged, so that they mutually repel, or a stable, often high-viscosity or even solid protective layer is formed around the droplets.

However, for the practical preparation of cosmetic or dermatological emulsions, the use of one or more emulsifiers on their own is generally insufficient. Important factors for the stability of cosmetic or dermatological preparations are also:

very fine distribution of the two phases in one another:

the smaller the dispersed particles, the more stable the emulsion.

high viscosity of the outer phase a stable interfacial film a balanced phase volume ratio The emulsifier system must therefore in most cases comprise, in addition to the actual emulsifier, a further component which is referred to as coemulsifier, stabilizer or, depending on the activity mechanism, also as bodying agent, thickener or protective colloid etc.

These substances, which for the sake of simplicity are referred to below as stabilizers, increase the stability of an emulsion. Stabilizers must not be interface-active, but can be amphiphilically constructed compounds.

One way of stabilizing emulsions is, in accordance with that stated above, to increase the viscosity of the outer phase. This viscosity increase generally brings about a considerable reduction in the mobility of the dispersed droplets, as a result of which the rate of sedimentation or creaming is reduced. As a result of this, the droplets also meet less frequently, which results in a lower tendency toward coalescence.

The viscosity of the external phase can, for example, be increased by adding thickeners which form, for example, gels and/or lamellar liquid crystals. In principle, emulsifiers are also able to increase the viscosity of a liquid as a result of the formation of emulsifier gel networks. However, this requires a relatively large amount of emulsifier since gel networks are only formed when the total interface between the phases is coated with emulsifier molecules.

The breaking of an emulsion can also be prevented by the choice of a suitable phase volume ratio. To illustrate this fact, imagine an emulsion as a system of metal spheres of equal diameter (internal phase) and a liquid (external phase). Sedimentation or creaming can, in this simple model, no longer occur if the entire liquid is filled with metal spheres. Assuming as dense as possible a sphere packing as distribution, this is the case precisely at a ratio of 1:2, i.e. when ⅔ of the emulsion consists of an internal phase. It is obvious that the viscosity of an emulsion increases as the proportion of internal phase grows since the mobility of the dispersed droplets becomes restricted as a result.

The person skilled in the art is of course aware of the large number of options for formulating stable emulsions, i.e. multiphase systems of oil components and water in addition to further auxiliaries and additives for cosmetic or dermatological use, for example in the form of creams and ointments, which are spreadable in the range from room to skin temperature, or as lotions and milks, which are flowable in this temperature range. In this connection, as well as the choice of the "correct" emulsifier or emulsifier system, the further composition of the preparation, in particular, is important.

Emulsions of "liquid" (=flowable) consistency are used in cosmetics, for example as care, cleansing, face or hand lotions. They generally have a viscosity of from about 2 000 mPa·s to about 10 000 mPa·s. The stability of flowable emulsions requires particular attention since the considerably greater mobility of the particles encourages more rapid coalescence.

Disadvantages can, for example, lie in the fact that relatively large amounts of one or more emulsifiers are required (e.g. 3% by weight or more). Since, however, even emulsifiers, like ultimately every chemical substance, can in individual cases trigger allergic reactions or reactions based on hypersensitivity of the user (although the use of customary cosmetic emulsifiers is of course generally entirely acceptable), it is desirable to keep the emulsifier content of a cosmetic or dermatological formulation as low as possible.

Emulsions with a very low viscosity (low-viscosity or sprayable emulsions) have hitherto, in accordance with that stated above, only been able to be formulated with considerable effort, if at all. Accordingly, the supply of such formulations is extremely low. Nevertheless, such formulations could offer the consumer cosmetic results which are hitherto unknown.

SUMMARY OF THE INVENTION

An object of the present invention was therefore to overcome the disadvantages of the prior art.

In particular, the aim was to provide cosmetic or dermatological preparations in which the use of oils of a conventional type can be dispensed with entirely. In addition, the aim was to find oil-free cosmetic or dermatological light protection preparations which permit, for example, the formulation of high sun protection factors.

In addition, it was an object of the invention to develop cosmetic and dermatological bases for cosmetic and dermatological preparations which are characterized by good skin compatibility.

It was a further object of the invention to prepare preparations of the emulsion type which have a low or very low viscosity and do not have the disadvantages of the prior art. A further object of the invention was to discover solutions for cosmetic or dermatological, in most cases low-viscosity, emulsions which are stable toward increased electrolyte concentrations.

Admittedly, the prior art recognizes, as oil-free formulations, gels, namely hydrogels, which are dimensionally stable, readily deformable disperse systems of at least two components. Gels in most cases comprise a solid, colloidally distributed substance with long or heavily branched particles (e.g. gelatin, silica, montmorillonite, bentonites, polysaccharides, pectins etc., gelling agents often referred to as thickeners) and a liquid (in most cases water) as dispersant. The thickener forms a three-dimensional network in the dispersant, which may be so strong that, for example, hydrogels consist of almost 100% of water (in addition to e.g. about 0.2 to 1.0% of a gelling agent) and in this connection may have an entirely solid consistency.

However, the prior art was unable to point the way to the present invention.

It was surprising and could in no way have been foreseen by the person skilled in the art that all of these objects are achieved by oil-free cosmetic or dermatological emulsions which comprise a water phase and at least one UV filter substance which is liquid at room temperature as a further phase, where the difference in density between the UV filter phase and the water phase (determinable using a computerized digital density meter of the type DMA 45 from chempro/PA at 25° C.) is not greater than 0.01 g·cm$^{-3}$, and which optionally comprise further cosmetic or pharmaceutical auxiliaries, additives and/or active ingredients.

On the basis of the preparations according to the invention, it is possible to formulate cosmetic and dermatological preparations, in particular light protection preparations, preferably with a high sun protection factor, which are completely satisfactory preparations in every respect, which suprisingly exhibit excellent cosmetic properties and are characterized by excellent skin compatibility.

The preparations according to the invention represent an enrichment of the prior art in every respect with regard to O/W emulsions, in particular with regard to flowable or sprayable O/W emulsions.

In addition, by the process according to the invention, very stable O/W formulations, for example sprayable formulations with a high sun protection factor, are obtainable in a surprisingly simple manner.

The preparations according to invention can be used as a base for cosmetic or dermatological formulations. These may have the customary composition and be used, for example, for the treatment and the care of the skin or as light protection preparation. For use, the cosmetic and dermatological preparations according to the invention are applied to the skin in a sufficient amount in the manner customary for cosmetics.

The formulations according to the invention are stabilized by matching the density of the UV filter phase and the water phase. It was particularly surprising that the preparations according to the invention are extremely stable even without the addition of further stabilizers, such as, for example, bodying agents, thickeners or protective colloids etc. In particular, this could in no way have been foreseen for flowable or even sprayable formulations.

DETAILED DESCRIPTION OF THE PREFERRED EMBODIMENTS

Particularly advantageous UV filter substances which are liquid at room temperature for the purposes of the present invention are homomenthyl salicylate, 2-ethylhexyl-2-cyano-3,3-diphenylacrylate, 2-ethylhexyl-2-hydroxybenzoate and esters of cinnamic acid, preferably 2-ethylhexyl 4-methoxycinnamate and isopentyl 4-methoxycinnamate.

Homomenthyl salicylate (INCl: Homosalate) is characterized by the following structure:

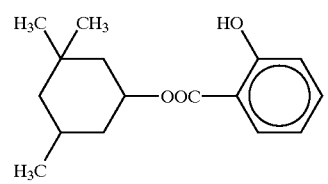

2-Ethylhexyl-2-cyano-3,3-diphenylacrylate (INCl: Octocrylene) is available from BASF under the name Uvinul® N 539 and is characterized by the following structure:

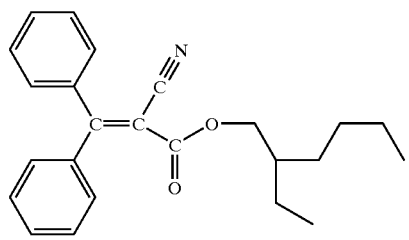

2-Ethylhexyl-2-hydroxybenzoate (2-ethylhexyl salicylate, octyl salicylate, INCl: Octyl Salicylate) is available, for example, from Haarmann & Reimer under the trade name Neo Heliopan OS and is characterized by the following structure:

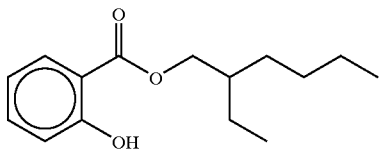

2-Ethylhexyl 4-methoxycinnamate (INCI: Octyl Methoxycinnamate) is available, for example, from Hoffmann-La Roche under the trade name Parsol MCX and is characterized by the following structure:

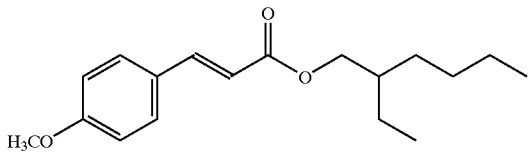

Isopentyl 4-methoxycinnamate (INCI: Isoamyl p-Methoxycinnamate) is available, for example, from Haarmann & Reimer under the trade name Neo Heliopan E 1000 and is characterized by the following structure:

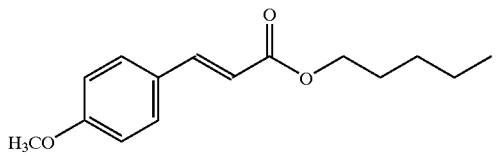

The total amount of one or more UV filter substances which are liquid at room temperature in the finished cosmetic or dermatological preparations is advantageously chosen from the range 0.1% by weight to 30% by weight, preferably from 0.5 to 20% by weight, in each case based on the total weight of the preparations.

The preparations according to the invention can further advantageously, although not obligatorily, also comprise silicone oils and/or silicone waxes. Silicone oils are high molecular weight synthetic polymeric compounds in which silicon atoms are linked in a chain-like and/or network-like manner via oxygen atoms, and the remaining valences of the silicon are saturated by hydrocarbon radicals (in most cases methyl, less often ethyl, propyl, phenyl groups etc.). Systematically, the silicone oils are referred to as polyorganosiloxanes; the methyl-substituted polyorganosiloxanes, which represent the most significant compounds of this group in terms of number and are characterized by the following structural formula

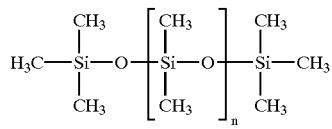

are also referred to as polydimethylsiloxane or Dimethicone (INCI). There are dimethicones with various chain lengths and with various molecular weights.

For the purposes of the present invention, particularly advantageous polyorganosiloxanes are, for example, dimethylpolysiloxanes [poly(dimethylsiloxane)], which are available, for example, under the trade names Abil 10 to 10 000 from Th. Goldschmidt. Also advantageous are phenyl-methylpolysiloxanes (INCI: Phenyl Dimethicone, Phenyl Trimethicone), cyclic silicones (Octamethylcyclotetrasiloxane or Decamethylcyclopentasiloxane), which are also referred to as Cyclomethicones in accordance with INCI, amino-modified silicones (INCI: Amodimethicone) and silicone waxes, e.g. polysiloxane-polyalkylene copolymers (INCI: Stearyl Dimethicone and Cetyl Dimethicone) and dialkoxy-dimethylpolysiloxanes (Stearoxy Dimethicone and Behenoxy Stearyl Dimethicone), which are available as various Abil wax grades from Th. Goldschmidt.

Cosmetic and dermatological preparations according to the invention may be in various forms. First, for example, they may be an O/W emulsion or O/W microemulsion, a multiple emulsion (e.g. a W/O/W emulsion), a sprayable emulsion or else a foam.

For the purposes of the present invention, the term "emulsion" is to be understood as meaning a preparation which, in addition to at least one water phase, comprises one or more liquid UV filters according to the invention as a further phase (so to speak as the "oil phase"). This UV filter phase can advantageously comprise, dissolved therein, solid UV filter substances and optionally, but not obligatorily, silicone oils and/or silicone waxes. Emulsions according to the invention are stabilized by matching the density of the phases.

Accordingly, the invention also provides a process for the preparation of oil-free cosmetic or dermatological emulsions, which involves at least one UV filter substance which is liquid at room temperature being a phase of the preparation and matching the density of the water phase to the density of this UV filter phase in such a way that the difference in density between the two phases (determinable using a computerized digital density meter of the DMA45 type from chempro/PA at 25° C.) is not greater than 0.01 g cm$^{-3}$.

According to the invention, the density of the water phase is advantageously matched to the density of the UV filter phase by adding one or more electrolytes.

According to the invention, the electrolyte(s) is/are advantageously chosen from the following groups:

1) Water-soluble UV filter substances:
   i.e. water-soluble UV filter substances which are mostly present as alkali metal salts, in particular those which carry one or more sulfonic acid groups or sulfonate groups on their molecular backbone.

Examples of advantageous water-soluble UV filter substances are:
   salts of 2-phenylbenzimidazole-5-sulfonic acid, such as its sodium, potassium or its triethanolammonium salt, in particular the phenylene-1,4-bis(2-benzimidazyl)-3, 3'-5,5'-tetrasulfonic acid bis-sodium salt and the sulfonic acid itself:
   sulfonic acid derivatives of 3-benzylidenecamphor, such as, for example, 4-(2-oxo-3-bornylidenemethyl) benzenesulfonic acid and/or 2-methyl-5-(2-oxo-3-bornylidenemethyl)sulfonic acid and salts thereof, for example the corresponding sodium, potassium or tri-ethanolammonium salt,
   sulfonic acid derivatives of benzophenones, preferably 2-hydroxy-4-methoxybenzophenone-5-sulfonic acid and its salts, for example the corresponding sodium, potassium or triethanolammonium salt,
   1,4-di(2-oxo-10-sulfo-3-bornylidenemethyl)benzene and salts thereof (the corresponding 10-sulfato compounds, for example the corresponding sodium, potassium or triethanolammonium salt), also referred to as benzene-1,4-di(2-oxo-3-bornylidenemethyl-10-sulfonic acid, which is characterized by the following structure:

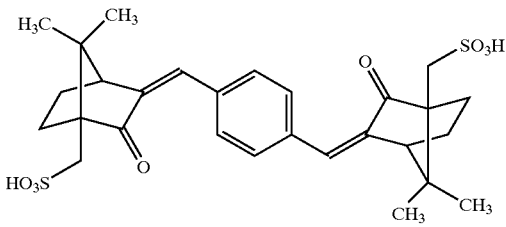

2) Salts with the following anions:

chlorides, and also inorganic oxo element anions, and of these in particular sulfates, carbonates, phosphates, borates and aluminates. Electrolytes based on organic anions are also advantageous, e.g. lactates, acetates, benzoates, propionates, tartrates, citrates, amino acids and salts thereof and others besides. Comparable effects can also be achieved by ethylenediaminetetraacetic acid and salts thereof.

The cations of these salts used are preferably ammonium, alkylammonium, alkali metal, alkaline earth metal, magnesium, iron and zinc ions. It does not need to be mentioned that only physiologically acceptable electrolytes should be used in cosmetics. Particular preference is given to potassium chloride, sodium chloride, magnesium sulfate, zinc sulfate and mixtures thereof.

3) Amino acids and salts thereof or anions thereof:

Amino acids are a constituent of the natural moisturizing factor. The addition of amino acids, in particular essential amino acids, is to be regarded as advantageous since moisture can be bound in the skin by means of hydration processes.

Amino acids having particularly advantageous cosmetic or dermatological action are glycine, alanine, valine, leucine, isoleucine, phenylalanine, tyrosine, proline, hydroxyproline, serine, threonine, cysteine, methionine, tryptophan, arginine.

4) Cosmetically and dermatologically relevant α-hydroxycarboxylic acids, α-ketocarboxylic acids and β-hydroxycarboxylic acids, and, in particular, salts thereof, where the cations can advantageously be chosen from the group consisting of ammonium ions, alkylammonium ions, alkali metal ions, alkaline earth metal ions, magnesium ions, iron ions or zinc ions.

α-Hydroxycarboxylic acids which are advantageous according to the invention conform to the general formula

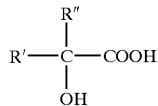

β-Hydroxycarboxylic acids which are advantageous according to the invention conform to the general formula

α-Ketocarboxylic acids which are advantageous according to the invention conform to the general formula

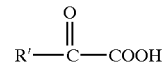

where, in each case, R' and R", independently of one another, are chosen from the groups (a) H,
(b) branched or unbranched $C_{1-25}$-alkyl,
(c) branched or unbranched $C_{1-25}$-alkyl substituted by one or more carboxyl groups and/or hydroxyl groups and/or aldehyde groups and/or oxo groups (keto groups)
(d) phenyl,
(e) phenyl substituted by one or more carboxyl groups and/or hydroxyl groups and/or branched and/or unbranched $C_{1-25}$-alkyl groups,
  or where the α-carbon atom and the β-carbon atom of the β-hydroxycarboxylic acid with R' and R" together forms an
(f) unsubstituted cycloalkyl group or aryl group having 3 to 7 ring atoms or a
(g) cycloalkyl group or aryl group having 3 to 7 ring atoms and substituted by one or more carboxyl groups and/or hydroxyl groups and/or oxo groups (keto groups) and/or branched and/or unbranched $C_{1-25}$-alkyl groups and where the α-hydroxycarboxylic acids or the β-hydroxycarboxylic acids or the α-ketocarboxylic acids can optionally be present in the form of their physiologically compatible salts.

The α-hydroxycarboxylic acids according to the invention are advantageously chosen from the following classes of substance (where they are also listed as representatives of their salts or anions):

α-hydroxy fatty acids, where these in turn are particularly advantageously chosen from the group of $C_{10-18}$-alkylcarboxylic acids, in particular α-hydroxycarboxylic acids according to the formula

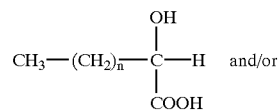

α-hydroxyisocarboxylic acids according to the formula

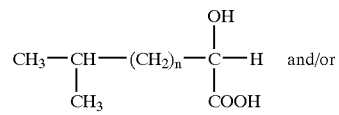

α-hydroxyanteisocarboxylic acids according to the formula

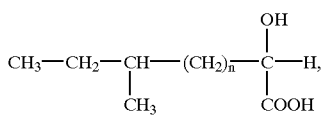

where n is in each case a number below 7,

α-hydroxy sugar acids, aliphatic α-hydroxy fruit acids, very particularly maleic acid, lactic acid, citric acid, tartaric acid, unsubstituted aromatic α-hydroxycarboxylic acids (e.g. mandelic acid) or substituted aromatic α-hydroxycarboxylic acids.

It is also advantageous to use mixtures of aliphatic α-hydroxycarboxylic acids, in particular in the form of wool wax acid mixtures in which the content of α-hydroxycarboxylic acids is 20 to 30% by weight, based on the total composition.

Preferred α-ketocarboxylic acid is pyruvic acid (α-oxopropanoic acid).

The total amount of one or more electrolytes in the finished cosmetic or dermatological preparations is chosen so that the density of the water phase is matched to the density of the UV filter phase in such a way that the difference in density between the two phases (determinable using a computerized digital density meter of the DMA 45 type from chempro/PA at 25° C.) is not greater than 0.01 g·cm$^{-3}$. This amount can be readily determined by simple experimentation without intrinsic inventive activity.

Emulsions according to the invention preferably comprise one or more emulsifiers customary for these formulations.

The emulsifier(s) is/are advantageously chosen from the group consisting of the following compounds:

polyglyceryl-2 dipolyhydroxystearate, PEG-30 dipolyhydroxystearate, cetyidimethicone copolyol, glycol distearate, glycol dilaurate, diethylene glycol dilaurate, sorbitan trioleate, glycol oleate, glyceryl dilaurate, sorbitan tristearate, propylene glycol stearate, propylene glycol laurate, propylene glycol distearate, sucrose distearate, PEG-3 castor oil, pentaerythrityl monostearate, pentaerythrityl sesquioleate, glyceryl oleate, glyceryl stearate, propylene glycol stearate, glyceryl diisostearate, pentaerythrityl monooleate, sorbitan sesquioleate, isostearyl diglyceryl succinate, glyceryl caprate, palm glycerides, glyceryl stearate, cholesterol, lanolin, lanolin alcohols, glyceryl oleate (containing 40% monoester), polyglyceryl-2 sesquiisostearate, polyglyceryl-2 sesquioleate, PEG-20 sorbitan beeswax, sorbitan oleate, sorbitan isostearate, trioleyl phosphate, glyceryl stearate and ceteareth-20 (Teginacid from Th. Goldschmidt), sorbitan stearate, sorbitan isostearate, PEG-7 hydrogenated castor oil, steareth-2, oleth-2, cetyl alcohol and ceteareth-30 (emulsifier E 2209 from Th. Goldschmidt), PEG-5soya sterol, PEG-6 sorbitan beeswax, ceteth-2, glyceryl stearate SE, methylglucose sesquistearate, PEG-10 hydrogenated castor oil, sucrose distearate, oleth-3, sorbitan palmitate, PEG-22/dodecyl glycol copolymer, polyglyceryl-2 PEG-4 stearate, laneth-5, ceteth-3, laureth-3, ceteareth-3, stearyl alcohol and steareth-7 and steareth-10 (emulsifier E-2155 from Th. Goldschmidt), oleth-5, sorbitan laurate, laureth4, PEG-4 laurate, polysorbate 61, polysorbate 81, beheneth-10, polysorbate 65, polysorbate 80, laneth-10, triceteareth-4 phosphate, triceteareth-4 phosphate and sodium $C_{14-17}$-alkyl sec sulfonate (Hostacerin CG from Hoechst), PEG-8 stearate, glyceryl stearate and PEG-100 stearate (Arlacel 165 from ICI), polysorbate 85, trilaureth-4 phosphate, PEG-25 glyceryl trioleate, oleth-10, steareth-10, ceteth-10, PEG-35 castor oil, sucrose stearate, PEG-8 oleate, trioleth-8 phosphate, PEG-40 sorbitan lanolate, PEG-15 glyceryl ricinoleate, choleth-24 and ceteth-24 (Solulan C-24 from Amerchol), $C_{1215}$-Pareth-12, PEG-20 glyceryl isostearate, polysorbate 60, PEG-40 hydrogenated castor oil, PEG-16 soya sterol, PEG-20 glyceryl oleate, PEG-20 stearate, polysorbate 80, PEG-20 methylglucose sesquistearate, PEG-30 glyceryl isostearate, PEG-20 glyceryl laurate, ceteth-20, ceteareth-25, PEG-30 stearate, PEG-30 glyceryl stearate, polysorbate 20, laureth-23, PEG-40 stearate, PEG-30 glyceryl laurate, PEG-50 stearate, PEG-100 stearate, PEG-150 laurate, polyglyceryl-3 methylglucose distearate, ceteareth-12, ceteareth-20 and steareth-21.

In addition, the emulsifier(s) is/are preferably chosen from the group of fatty acids which are completely or partially neutralized with customary alkalis (such as, for example, sodium and potassium hydroxide, sodium and potassium carbonate, and mono- and triethanolamine). Particularly advantageous are, for example, stearic acid and stearates, isostearic acid and isostearates, palmitic acid and palmitates, and also myristic acid and myristates.

Moreover, it is advantageous for the purposes of the present invention to choose the emulsifier(s) from the group of fatty alcohols which have a chain length of more than 8 carbon atoms. Particular preference is given, for example, to cetyl, stearyl, myristyl and behenyl alcohol.

For the purposes of the present invention, it is advantageous to choose the emulsifier content (one or more compounds) from the range 0.5% by weight to 7% by weight.

The list of said emulsifiers which can be used for the purposes of the present invention is of course not intended to be limiting.

The preparations according to the invention can, moreover, also comprise hydrocolloids, for example in order to adjust the viscosity.

Examples of advantageous hydrocolloids are:

organic, natural compounds, such as, for example, agar agar, carrageen, tragacanth, gum arabic, alginates, pectins, polyoses, guar gum, carob bean flower, starch, dextrins, gelatins, casein, organic, modified natural substances, such as, for example, carboxymethylcellulose and other cellulose ethers, hydroxyethyl- and -propylcellulose and the like, organic, completely synthetic compounds, such as, for example, polyacrylic and polymethacrylic compounds, vinyl polymers, polycarboxylic acids, polyethers, polyimines, polyamides, inorganic compounds, such as, for example, polysilicic acids, clay minerals, such as montmorillonites, zeolites, silicas.

Examples of further hydrocolloids which are preferred according to the invention are methylcelluloses, which is the name for the methyl ethers of cellulose. They are characterized by the following structural formula

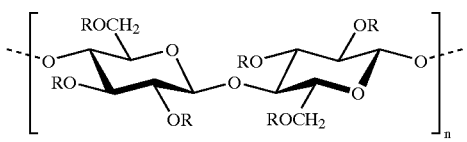

in which R can be a hydrogen or a methyl group.

Particularly advantageous for the purposes of the present invention are the cellulose mixed ethers, which are generally likewise referred to as methylcelluloses, which contain, in addition to a dominating content of methyl groups, also 2-hydroxyethyl, 2-hydroxypropyl or 2-hydroxybutyl groups. Particular preference is given to (hydroxypropyl) methylcelluloses, for example those available under the trade name Methocel E4M from Dow Chemical Comp.

Also advantageous according to the invention is sodium carboxymethylcellulose, the sodium salt of the glycolic ether of cellulose, for which R in structural formula I can be a hydrogen and/or $CH_2$—COONa. Particular preference is given to the sodium carboxymethylcellulose available under the trade name Natrosol Plus 330 CS from Aqualon and also referred to as cellulose gum.

Also preferred for the purposes of the present invention is xanthan (CAS No. 11138-66-2), also called xanthan gum, which is an anionic heteropolysaccharide which is generally formed by fermentation from maize sugar and is isolated as the potassium salt. It is produced by Xanthomonas campestris and some other species under aerobic conditions with a molecular weight of $2 \times 10^6$ to $24 \times 10^6$. Xanthan is formed from a chain having β-1,4-bonded glucose (cellulose) with side chains. The structure of the subgroups ("repeat units") consists of glucose, mannose, glucuronic acid, acetate and pyruvate.

Other hydrocolloids which are advantageous according to the invention are polymers of acrylic acid, in particular those chosen from the group of carbomers or Carbopols (Carbopol® is actually a registered trade mark of the B. F. Goodrich Company). Carbopols are compounds of the general structural formula

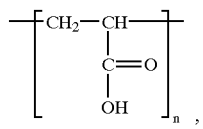

whose molecular weight can be between about 4,00,000 and more than 4,000,000. The group of Carbopols also includes acrylate-alkyl acrylate copolymers, for example those characterized by the following structure:

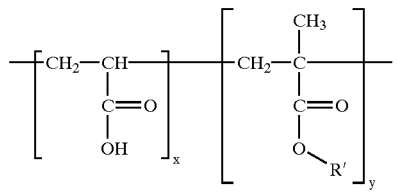

where R' is a long-chain alkyl radical, and x and y are numbers which symbolize the respective stoichiometric content of each comonomer. These Carbopols, too, are advantageous for the purposes of the present invention. Examples of advantageous Carbopols are the grades 907, 910, 934, 940, 941, 951, 954, 980, 981, 1342, 1382, 2984 and 5984, it being possible for these compounds to be present individually or in any combinations with one another. Particular preference is given to Carbopol 981, 1382 and 5984 (either individually or in combination with other hydrocolloids).

Also advantageous for the purposes of the present invention are the copolymers, comparable with the acrylate-alkyl acrylate copolymers, of $C_{10-30}$-alkyl acrylates and one or more monomers of acrylic acid, of methacrylic acid or esters thereof. The INCI name for such compounds is "Acrylates/C 10-30 Alkyl Acrylate Crosspolymer". Particularly advantageous are those available under the trade names Pemulen TR1 and Pemulen TR2 from B. F. Goodrich Company.

The total amount of one or more hydrocolloids in the finished cosmetic or dermatological emulsions is advantageously chosen to be less than 1.0% by weight, preferably between 0.01 and 0.5% by weight, based on the total weight of the preparations.

The water phase of the preparations according to the invention can advantageously comprise customary cosmetic auxiliaries, such as, for example, alcohols, polyols, polymers, foam stabilizers, electrolytes and moisturizers.

Moisturizers is a term used to describe substances or mixtures of substances which, following application or distribution on the surface of the skin, confer on cosmetic or dermatological preparations the property of reducing moisture loss by the horny layer (also called transepidermal water loss (TEWL)) and/or having a beneficial effect on the hydration of the horny layer.

Advantageous moisturizers for the purposes of the present invention are, for example, gycerol, lactic acid, pyrrolidonecarboxylic acid and urea. In addition, it is particularly advantageous to use polymeric moisturizers from the group of water-soluble and/or water-swellable and/or water-gellable polysaccharides. Particularly advantageous are, for example, hyaluronic acid, chitosan and/or a fucose-rich polysaccharide, which is listed in Chemical Abstracts under the registry number 178463-23-5 and is available, for example, under the name Fucogel®1000 from SOLABIA S.A.

Depending on their composition, cosmetic or topical dermatological compositions can be used, for example, for the purposes of the present invention as skin protection cream, cleansing milk, sunscreen lotion, day or night cream etc. It is optionally possible and advantageous to use the compositions according to the invention as a basis for pharmaceutical formulations.

The cosmetic and dermatological preparations according to the invention can also comprise cosmetic auxiliaries, as are customarily used in such preparations, e.g. preservatives, bactericides, perfumes, antifoams, dyes, pigments which have a coloring action, emollients, moisturizers and/or humectants or other customary constituents of a cosmetic or dermatological formulation.

According to the invention, the preparations advantageously comprise one or more antioxidants. Favorable, but nevertheless optional, antioxidants which can be used are all antioxidants customary or suitable for cosmetic and/or dermatological applications. Here, it is advantageous to use antioxidants as a single class of active ingredient if a cosmetic or dermatological application is at the fore, such as, for example, control of the oxidative stress of the skin. It is, however, also favorable to provide the preparations according to the invention with a content of one or more antioxidants if the preparations are to serve another purpose, e.g. as sunscreens.

The antioxidants are particularly advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g. buthionine sulfoximines, homocysteine sulfoximine, buthionine sulfones, penta-, hexa-, heptathionine sulfoximines) in very low tolerated doses (e.g. pmol to µmol/kg), and also (metal) chelating agents (e.g. α-hydroxyfatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate) and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide), and the derivatives (salts, esters, ethers, sugars, nucleotides, nucleosides, peptides and lipids) of said active substances which are suitable according to the invention.

The amount of the abovementioned antioxidants (one or more compounds) in the preparations according to the invention is preferably 0.001 to 30% by weight, particularly preferably 0.05-20% by weight, in particular 0.1-10% by weight, based on the total weight of the preparation.

If vitamin E and/or derivatives thereof are the antioxidant(s), it is advantageous to choose the respective concentrations thereof from the range 0.001-10% by weight, based on the total weight of the formulation.

If vitamin A, or vitamin A derivatives, or carotenes or derivatives thereof are the antioxidant(s), it is advantageous to choose the respective concentrations thereof from the range 0.001-10% by weight, based on the total weight of the formulation.

The list of said active ingredients or active ingredient combinations which can be used in the preparations according to the invention is not of course intended to be limiting.

In a particularly advantageous embodiment, the present invention further provides a process for the preparation of oil-free cosmetic or dermatological emulsions, which comprises dissolving at least one UV filter substance which is solid at room temperature in at least one UV filter substance which is liquid at room temperature, and matching the density of the water phase to the density of this UV filter phase in such a way that the difference in density between the two phases (determinable using a computerized digital density meter of the type DMA 45 from chempro/PA at 25° C.) is not greater than 0.01 $g \cdot cm^{-3}$.

Accordingly, both cosmetic and dermatological preparations which are in the form of a sunscreen are particularly favorable. In addition to the active ingredients according to the invention, these additionally comprise further UV-A and/or UV-B filter substances. The further UV filter substances are preferably incorporated into the UV filter phase in accordance with the process according to the invention. Such formulations can, but do not necessarily, optionally also comprise one or more inorganic pigments as UV filter substances.

Preference is given to inorganic pigments based on metal oxides and/or other metal compounds which are insoluble or sparingly soluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides.

For the purposes of the present invention, it is also advantageous to provide those cosmetic and dermatological preparations whose main purpose is not protection against sunlight, but which nevertheless have a content of UV protection substances. Thus, for example, UV-A and UV-B filter substances are usually incorporated into day creams.

UV protection substances, like antioxidants and, if desired, preservatives, also represent effective protection of the preparations themselves against decay.

Preparations according to the invention advantageously comprise further substances which absorb UV radiation in the UV-B region, where the total amount of filter substances is, for example, 0.1% by weight to 30% by weight, preferably 0.5 to 20% by weight, in particular 1.0 to 15.0% by weight, based on the total weight of the preparations, in order to make available cosmetic preparations which protect the hair and/or the skin from the entire range of ultraviolet radiation. They can also be used as sunscreens for the hair or the skin.

Advantageous further UV-A filter substances for the purposes of the present invention are dibenzoylmethane derivatives, in particular 4-(tert-butyl)-4'methoxydibenzoylmethane (CAS No. 70356-09-1), which is sold by Givaudan under the name Parsol® 1789 and by Merck under the trade name Eusolex® 9020.

Advantageous UV filter substances for the purposes of the present invention are also "broad-band" filters, i.e. filter substances which absorb both UV-A and UV-B radiation.

Advantageous broad-band filters or UV-B filter substances are, for example, bisresorcinyltriazine derivatives having the following structure:

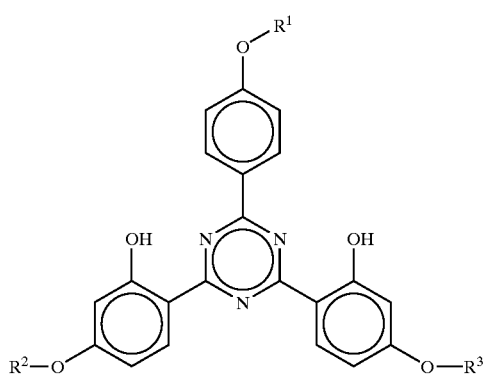

where $R^1$, $R^2$ and $R^3$, independently of one another, are chosen from the group of branched and unbranched alkyl groups having 1 to 10 carbon atoms, or are a single hydrogen atom. Particular preference is given to 2,4-bis{[4-(2-ethylhexyloxy)-2-hydroxy]phenyl}-6-(4-methoxyphenyl)-1,3,5-triazine (INCI: Aniso Triazine), which is available under the trade name Tinosorb® S from CIBA-Chemikalien GmbH, and to tris(2-ethylhexyl) 4,4′,4″-(1,3,5-triazine-2,4,6-triyltriimino)trisbenzoate, synonym: 2,4,6-tris[anilino-(p-carbo-2′-ethyl-1′hexyloxy)]-1,3,5-triazine (INCI: Octyl Triazone), which is marketed by BASF Aktiengesellschaft under the trade name UVINUL® T 150.

Other UV filter substances which have the structural formula

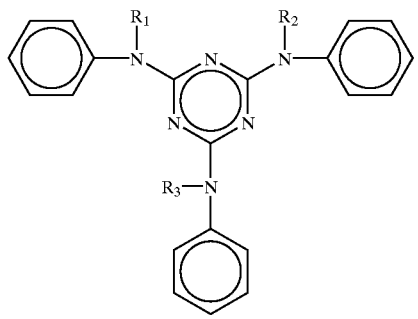

are also advantageous UV filter substances for the purposes of the present invention, for example the s-triazine derivatives described in European laid-open specification EP 570 838 A1, whose chemical structure is expressed by the generic formula

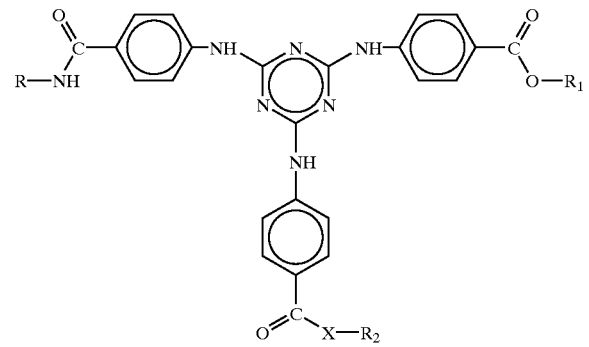

where

R is a branched or unbranched $C_1$-$C_{18}$-alkyl radical, a $C_5$-$C_{12}$-cycloalkyl radical, optionally substituted with one or more $C_1$-$C_4$-alkyl groups, X is an oxygen atom or an NH group, $R_1$ is a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

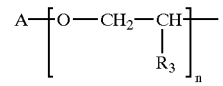

in which

A is a branched or unbranched $C_1$-$C_{18}$-alkyl radical, a $C_5$-$C_{12}$-cycloalkyl or aryl radical, optionally substituted by one or more $C_1$-$C_4$-alkyl groups, $R_3$ is a hydrogen atom or a methyl group, n is a number from 1 to 10, $R_2$ is a branched or unbranched $C_1$-$C_{18}$-alkyl radical, a $C_5$-$C_{12}$-cycloalkyl radical, optionally substituted by one or more $C_1$-$C_4$-alkyl groups, when X is the NH group, and a branched or unbranched $C_1$-$C_{18}$-alkyl radical, a $C_5$-$C_{12}$-cycloalkyl radical, optionally substituted by one or more $C_1$-$C_4$-alkyl groups, or a hydrogen atom, an alkali metal atom, an ammonium group or a group of the formula

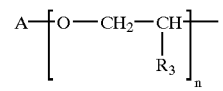

in which

A is a branched or unbranched $C_1$-$C_{18}$-alkyl radical, a $C_5$-$C_{12}$-cycloalkyl or aryl radical, optionally substituted by one or more $C_1$-$C_4$-alkyl groups, $R_3$ is a hydrogen atom or a methyl group, n is a number from 1 to 10, when X is an oxygen atom.

A particularly preferred UV filter substance for the purposes of the present invention is also an unsymmetrically substituted s-triazine, the chemical structure of which is expressed by the formula

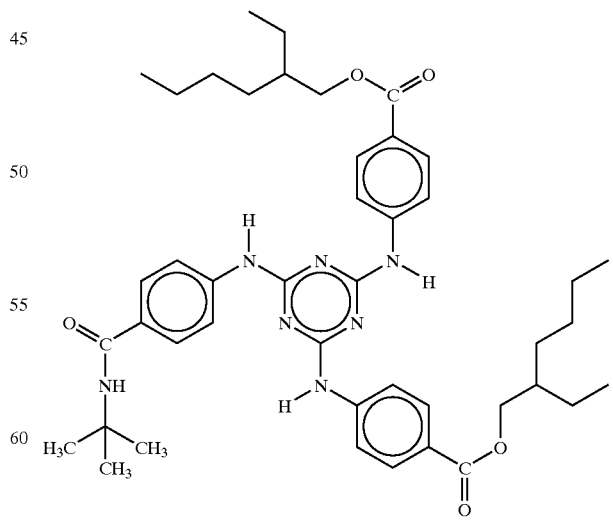

and which is also referred to below as dioctylbutylamidotriazone (INCI) and is available under the trade name UVA-SORB HEB from Sigma 3V.

European laid-open specification 775 698 also describes preferred bisresorcinyltriazine derivatives, the chemical structure of which is expressed by the generic formula

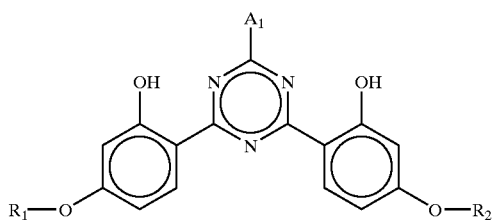

where $R_1$, $R_2$ and $A_1$ represent very different organic radicals.

Also advantageous for the purposes of the present invention are 2,4-bis{[4-(3-sulfonato)-2-hydroxypropyloxy)-2-hydroxy]phenyl}-6-(4-methoxyphenyl)-1,3,5triazine sodium salt, 2,4-bis{[4-(3-(2-propyloxy)-2-hydroxypropyloxy)-2-hydroxy]phenyl}-6-(4-methoxyphenyl)-1,3,5-triazine, 2,4-bis{[4-(2-ethylhexyloxy) -2-hydroxy]phenyl}-6-[4-(2-methoxyethylcarboxyl)phenylamino]-1,3,5-triazine, 2,4-bis{[4-(3-(2-propyloxy)-2-hydroxypropyloxy)-2-hydroxy]phenyl}-6-[4-(2-ethylcarboxyl)phenylamino]-1,3,5-triazine, 2,4-bis{[4-(2-ethylhexyloxy)-2-hydroxy]phenyl}-6-(1-methylpyrrol-2-yl)-1,3,5-triazine, 2,4-bis{[4-tris-(trimethylsiloxysilylpr -2-hydroxy]phenyl}-6-(4-methoxyphenyl)-1,3,5-triazine, 2,4-bis{[4-(2'-methylpropenyloxy)-2-hydroxy]phenyl}-6-(4-methoxyphenyl)-1,3,5-triazine and 2,4-bis{[4-(1',1',1',3',5',5',5'-heptamethylsiloxy -2"-methylpropyloxy)-2-hydroxy]phenyl}-6-(4-methoxyphenyl)-1,3,5-triazine.

An advantageous broad-band filter for the purposes of the present invention is 2,2'-methylenebis(6-(2H-benzotriazol-2-yl)4-(1,1,3,3-tetramethylbutyl)phenol), which is characterized by the chemical structural formula

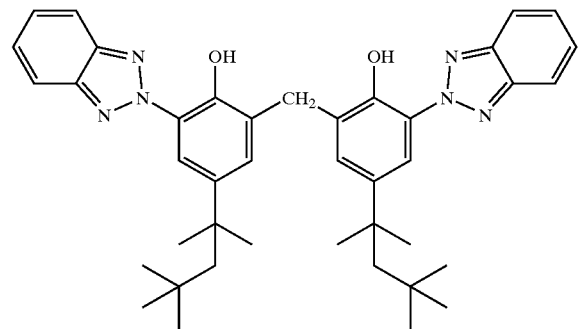

and is available under the trade name Tinosorb® M from CIBA-Chemikalien GmbH.

Another advantageous broad-band filter for the purposes of the present invention is 2-(2H-benzotriazol-2-yl)-4-methyl-6-[2-methyl-3-[1,3,3,3-tetramethyl-1-[(trimethylsilyl)oxy]disiloxanyl]propyl]phenol (CAS No.: 155633-54-8) having the INCI name Drometrizole Trisiloxane, which is characterized by the chemical structural formula

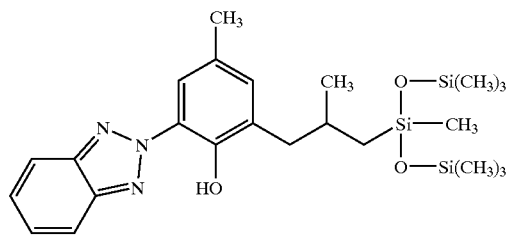

Examples of advantageous UV-B filter substances are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

2,4,6-trianilino(p-carbo-2'-ethyl-1'-hexyloxy)-1,3,5-triazine;

esters of benzalmalonic acid, preferably di(2-ethylhexyl) 4-methoxybenzalmalonate, derivatives of benzophenone, preferably 2-hydroxy-4-methoxybenzophenone, 2-hydroxy-4-methoxy4'-methylbenzophenone, 2,2'-dihydroxy-4-methoxybenzophenone and UV filters bonded to polymers.

It may also be of considerable advantage to use polymer-bound or polymeric UV filter substances in preparations according to the present invention, in particular those as are described in WO-A-92/20690.

In addition, it may in some instances be advantageous to incorporate further UV-A and/or UV-B filters according to the invention into cosmetic or dermatological preparations, for example certain salicylic acid derivatives, such as 4-isopropylbenzyl salicylate.

The list of said UV filters which can be used for the purposes of the present invention is not of course intended to be limiting.

The examples below serve to illustrate the present invention without limiting it. The numerical values in the examples are percentages by weight, based on the total weight of the respective preparations.

EXAMPLES

|  | 1 | 2 | 3 | 4 | 5 |
|---|---|---|---|---|---|
| Glyceryl stearate citrate | 0.5 | 0.5 |  | 0.5 |  |
| Glyceryl stearate |  |  | 0.5 | 0.5 | 0.5 |
| Dimethicone |  |  | 5 |  |  |
| Phenyltrimethicone |  |  | 5 | 5 |  |
| Cyclomethicone |  | 5 |  |  |  |
| Dioctylbutamidotriazone |  | 1 |  |  |  |
| Octyltriazone |  |  | 1 |  |  |
| Anisotriazine |  | 1 |  |  | 1 |
| Methylbenzylidenecamphor |  |  | 2 |  |  |
| Butylmethoxydibenzoylmethane |  |  |  | 2 |  |
| Octyl salicylate | 5 | 10 |  |  | 5 |
| Octyl methoxycinnamate | 5 | 5 | 10 | 2 | 5 |
| Octocrylene | 2 |  |  | 2 |  |
| Vitamin E acetate | 0.5 | 0.5 | 0.5 | 0.5 | 0.5 |
| Preservative | 0.7 | 0.7 | 0.7 | 0.7 | 0.7 |
| Carbomer |  |  | 0.1 | 0.2 |  |
| Xanthan gum | 0.05 |  |  |  | 0.2 |
| Glycerol | 12 | 10 | 15 | 2 | 15 |
| NaCl |  | 2 | 4 |  |  |

-continued

|  | 1 | 2 | 3 | 4 | 5 |
|---|---|---|---|---|---|
| Sodium phenylbenzimidazolesulfonate |  | 4 | 4 |  | 8 |
| Water | 74.25 | 60.2 | 50.1 | 87.8 | 64.3 |

What is claimed is:

1. An oil-free cosmetic or dermatological emulsion which comprises a water phase and at least one UV filter substance which is liquid at room temperature as a UV filter phase, where the difference in density between the UV filter phase and the water phase as determined using a computerized digital density meter of the type DMA 45 from Chempro/PA at 25° C. is not greater than 0.01 g·cm$^{-3}$.

2. The preparation as claimed in claim 1, further comprising one more compounds selected from the group consisting of cosmetic or pharmaceutical auxiliaries, additives and active ingredients.

3. The preparation an claimed in claim 1, which is in the form of a microemulsion, a multiple emulsion, a sprayable emulsion or a foam.

4. The preparation as claimed in claim 1, wherein the viscosity of the preparation is less than 10 000 mPa·s.

5. The preparation as claimed in claim 1, wherein the viscosity of the preparation is less than 2 000 mPa·s.

6. The preparation as claimed in claim 1, wherein the viscosity of the preparation is less than 1 500 mPa·s.

7. The preparation as claimed in claim 1, wherein the at least one liquid UV filter substance is present in an amount from 0.1% to 30% by weight, base on the total weight of the preparation.

8. The preparation as claimed in claim 1, wherein the at least one liquid UV filter substance is present in an amount from 0.5 to 20% by weight, based on the total weight of the preparation.

9. The preparation as claimed in claim 1, wherein the at least one liquid UV filter substance is selected from the group consisting of homomenthyl salicylato, 2-ethylhexyl-2-cyano-3,3-diphenylacrylate, 2-ethylhexyl-2-hydroxybenzoate, 2-ethyhexyl 4-methoxycinnamate and isopentyl 4-methoxycinnamate.

10. The preparation as claimed in claim 1, comprising one or more additives or active ingredients selected from the group consisting of antioxidants, UV filter substances and substances effective against acne.

11. The preparation as claimed in claim 1, further comprising one a more water-soluble UV filter substances.

12. The preparation as claim in claim 11, wherein the water-soluble UV filter substances are selected from the group consisting of the salts of 2-phenylbenzimidazole-5-sulfonic acid and the sulfonic acid derivatives of 3-benzylidenecamphor.

13. The preparation as claimed in claim 1, further comprising one or more inorganic micropigments which are suitable as UV filter substances.

14. The preparation as claimed in claim 13, wherein the inorganic micropigments are selected from the group consisting of the oxides of titanium ($TiO_2$), zinc (ZnO), iron, zirconium ($ZrO_3$), silicon ($SiO_2$), manganese, aluminum ($Al_2O_3$) and cerium.

15. A process for the preparation of an oil-free cosmetic or dermatological emulsion, which comprises combining water and at least one UV filter substance which is liquid at room temperature to produce a water phase and a UV filter phase and matching the density of the water phase to the density of the UV filter phase such that the difference in density between the two phases as determined using a computerized digital density meter of the type DMA 45 from Chempro/PA at 25° C. is not greater than 0.01 g·cm$^{-3}$.

16. The process according to claim 15, wherein the density of the water phase is matched to the density of the UV filter phase by adding one or more electrolytes.

17. The process according to claim 16, wherein the one or more electrolytes are selected from the group consisting of water-soluble UV filter substances; chloride, sulfate, carbonate, phosphate, borate, aluminate, lactates, acetate, propionate, tartrate and citrate salts; amino acids and salts or anions thereof; α-hydroxycarboxylic acids and salts thereof; α-ketocarboxylic acids and salts thereof; and β-hydroxycarboxylic acids and salts thereof.

18. A process for the preparation of oil-free cosmetic or dermatological emulsions, which comprises dissolving at least one UV filter substance which is solid at room temperature in at least one UV filter substance which is liquid at room temperature an matching the density of the water phase to the density of this UV filter phase in such a way that the difference in density between the two phases as determined using a computerized digital density meter of the type DMA 45 from Chempro/PA at 25° C. is not greater than 0.01 g·cm$^{-3}$.

19. The process according to claim 18, wherein the density of the water phase is matched to the density of the UV filter phase by adding one or more electrolytes.

20. The process according to claim 19, wherein the one or more electrolytes are selected from the group consisting of water-soluble UV filter substances; chloride, sulfate, carbonate, phosphate, borate, aluminate, lactates, acetate, propionate, tartrate and citrate salts; amino acids and salts or anions thereof; α-hydroxycarboxylic acids and salts thereof; α-ketocarboxylic acids and salts thereof; and β-hydroxycarhoxylic acids and salts thereof.

* * * * *

UNITED STATES PATENT AND TRADEMARK OFFICE
CERTIFICATE OF CORRECTION

PATENT NO. : 6,838,077 B2
DATED : January 4, 2005
INVENTOR(S) : Müller

It is certified that error appears in the above-identified patent and that said Letters Patent is hereby corrected as shown below:

Column 21,
Line 16, "g·cm $^{31\ 3}$" should read -- g·cm $^{-3}$ --;
Line 21, "an" should read -- as --;
Line 39, "salicylato" should read -- salicylate --.

Column 22,
Line 7, "(ZrO$_3$)" should read -- (ZrO$_2$) --;
Line 34, "an" should read -- and --.

Signed and Sealed this

Third Day of May, 2005

JON W. DUDAS
*Director of the United States Patent and Trademark Office*